United States Patent [19]
Maliszewski

[11] Patent Number: 5,198,342
[45] Date of Patent: Mar. 30, 1993

[54] DNA ENCODING IGA FC RECEPTORS

[75] Inventor: Charles R. Maliszewski, Seattle, Wash.

[73] Assignee: Immunex Corporation, Seattle, Wash.

[21] Appl. No.: 548,059

[22] Filed: Jul. 5, 1990

[51] Int. Cl.$^5$ .................. C12N 15/12; C07K 13/00
[52] U.S. Cl. ........................ 435/69.1; 435/252.3; 435/320.1; 530/350; 530/861; 536/23.5
[58] Field of Search ............. 435/69.1, 172.3, 320.1, 435/252.3; 530/350

[56] References Cited

U.S. PATENT DOCUMENTS 4,675,285  6/1987  Clark et al. ........................ 435/6

OTHER PUBLICATIONS

EMBO, J. 8:3667–3676, 1989, Gearing et al. Expression cloning of a receptor for human granulocyte-macroplage colony stimulating factor.
R.N.A.S. 84:8573–8577, 1987, Aruffo et al. Molecular cloning of a CD28 cDNA by a high-efficiency COS cell expression system.
Cell 47, 3–10, 1986, Yang et al. Human IL-3 (Multi-CSF): Identification by Expression Cloning of a Novel Hematopoietic Growth Factor Related to Murine IL-3.
Science 241:825–828, Yamasaki et al. Cloning and Expression of the Human Interleukin-6 (BSF-21/IFNβ2) Receptor.
DNA & Prof. Eng. Tech. 2:1–28, 1990, Cosman Expression Cloning of Cytotine Receptors by Screening Pools of CDNA Clones.
Cell: 47:657–665 1986, Kikutani et al. Molecular Structure of Human Lymphocyte Receptor for Immunoglobulin E.
EMBO J., 7:1053–1059, 1988, Stengels et al. Isolatioe and of DCNAs for two distinct human Fc receptors by ligand affinity cloning.
Eur. J. Immun., 18:621–626, Sep. 1988, Millet et al. Expression of receptors for IgA on mitogen-stimulated human lymphocytes.
Science, 241: 585–589, 29 Jul. 1988, Sims et al. CDNA Expression Cloning of the IL-1 Receptor, a Member of the Immunoglobulin Superfamily.
J. Immun. 143:4117–4122, 15 Dec. 1989, Shen et al. My43, a Monoclonal Antibody that Reacts with Human Myeloid Cells Inhibits Monocyte IgA Binding and Triggers Function.
P.N.A.S. 84:3365–3369, May 1987, Seed et al. Molecular cloning of the CD2 antigen, the T-cell erythrocyte receptor by a rapid immunoselection procedure.
Science, 238:1704–1707, 18 Dec. 1987, Smith et al. Blocking of HIV-1, Infectivity by a Soluble, Secreted Form of the CD4 Antigen.
Mestecky et al., "Immunoglobulin A (IgA): Molecular and Cellular Interactions Involves in IgA Biosynthesis and Immune Response," Advances in Immunology 40: 153, 1987.
Underdown et al., Ann. Rev. Immunol. 4:489, 1986 "Immunoglobulin A: Strategic Defense Initiative at the Mucosal Surface".
Fanger et al., "Subpopulations of human peripheral granulocytes and monocytes express receptors for IgA," Proc. Natl. Acad. Sci. 77:3640, 1980.
Gauldie et al., "Fc Receptors for IgA and Other Immunoglobulins on Resident and Activated Alveolar Macrophages," Molec. Immunol. 20:1029, 1983.
Maliszewski et al., "The Expression of Receptors for IgA on Human Monocytes and Calcitriol-treated HL-60 Cells," J. Immunol. 135:3878, 1985.
Chevaller, et al., "Immunofluorescence Analysis of IgA Binding by Human Mononuclear Cells in Blood and Lymphoid Tissue," J. Immunol. 142:2244, 1989.

(List continued on next page.)

Primary Examiner—Robert J. Hill, Jr.
Assistant Examiner—John D. Ulm
Attorney, Agent, or Firm—Patricia Anne Perkins; Christopher L. Wight

[57] ABSTRACT

The present invention provides an isolated DNA sequence encoding soluble and membrane bound forms of a mammalian IgA Fc receptor, as well as recombinant expression vectors and host cells suitable for expressing the protein.

11 Claims, 11 Drawing Sheets

OTHER PUBLICATIONS

Fanger et al., "Cytofluorographic Analysis of Receptors for IgA on Human Polymorphonuclear Cells and Monocytes and the Correlation of Receptor Expression with Phagocytosis," *Molec. Immunol* 20:1019, 1983.

Shen, et al., "IgA-Mediated Effector Function of HL-60 Cells Following Treatment with Calcitriol," *Molec. Immunol.* 23:611, 1986.

Ferreri et al., "Release of Leukotrienes $C_4$ and $B_4$ and Prostaglandin $E_2$ from Human Monocytes Stimulated with Aggregated IgA, IgA, and IgE," *J. Immunol.* 136:4188, 1986.

Albrechtson et al., Immunology 64:201, 1988 "Characterization of the IgA Receptor from Human Polymorphonuclear Leukocytes".

Monteiro et al., "Cellular Distribution, Regulation and Biochemical Nature of an Fc-alpha Receptor in Humans" *J. Exp. Med. 171:597, 1990.*

Kiyono et al., "Isotype-Specific Immunoregulation," *J. Exp. Med.* 161:731 (1985).

Bich-Thuy and Revillard, "Only T-alpha or T-gamma cells can be triggered by IgG or IgA to suppress the production of the matching Ig class," *Eur. J. Immunol.* 16:156, 1986.

Moore, et al., "Defective T Cell-Mediated, Isotype-Specific Immunoglobulin Regulation in B Cell Chronic Lymphocytic Leukemia," *Blood* 71:1012, 1988.

Dunkley, et al., Cognate T-cell help in the induction of IgA responses in vivo, *Immunology* 71:16, 1990.

Moore and Hoover, "Defective Isotype-Specific Regulation of IgA Anti-Erythrocyte Autoantibody-Forming Cells in NZB Mice," *J. Immunol.* 142:4282, 1989.

Yodoi et al., "Induction of FcR-alpha on Murine Lymphocytes by IgA in vitro," *J. Immunol.* 128:888, 1982.

Endoh et al., "Communications: IgA-Specific Helper Activity of T-alpha Cells in Human Peripheral Blood," *J. Immunol.* 127:2612, 1981.

Yodoi et al., "T-Cell Hybridomas Co-Expressing Fc Receptors (FcR) for Different Isotypes," *J. Immunol.* 131:303, 1983.

Adachi et al., "Murine IgA Binding Factors Produced by Fc-alphaR(+) T Cells: Role of Fc-gammaR(+) Cells for the induction of Fc-alphaR and Formation of IgA Binding Factor in Con A-Activated Cells," *J. Immunol.* 133:65, 1984.

Noro et al., "Murine IgA Binding Factors (IgA-BF) Suppressing IgA Production: Characterization and Target Specificity of IgA-BF," *J. Immunol.* 136:2910, 1986.

Hoover and Lynch, "Isotype-Specific Supression of IgA: Suppression of IgA Responses in BALB/c Mice by T-alpha Cells," *J. Immunol.* 130, 1983.

Word et al., "Regulation of IgA Expression by Isotype-Specific T Cells and Soluble Binding Factors," *Ann. Rev. Microbiol.* 40:503, 1986.

Shen and Fanger, "Secretory IgA Antibodies Synergize with IgG in Promoting ADCC by Human Polymorphonuclear Cells, Monocytes and Lymphocytes," *Cell* 59:75, 1981.

FcαR cDNA Structure

```
GGCACAGATC TTGGAACGAG ACGACCTGCT GTCAGCACG ATG GAC CCC AAA CAG ACC ACC CTC    64
                                          Met Asp Pro Lys Gln Thr Thr Leu     8

CTG TGT CTT GTG CTC TGT CTG GGC CAG AGG ATT CAG GCA CAG GAA GGG GAC TTT CCC   121
Leu Cys Leu Val Leu Cys Leu Gly Gln Arg Ile Gln Ala Gln Glu Gly Asp Phe Pro    27

ATG CCT TTC ATA TCT GCC AAA TCG AGT CCT GTG ATT CCC TTG GAT GGA TCT GTG AAA   178
Met Pro Phe Ile Ser Ala Lys Ser Ser Pro Val Ile Pro Leu Asp Gly Ser Val Lys    46

ATC CAG TGC CAG GCC ATT CGT GAA GCT TAC CTG ACC CAG CTG ATG ATC ATA AAA AAC   235
Ile Gln Cys Gln Ala Ile Arg Glu Ala Tyr Leu Thr Gln Leu Met Ile Ile Lys Asn    65

TCC ACG TAC CGA GAG ATA GGC AGA AGA CTG AAG TTT TGG AAT GAG ACT GAT CCT GAG   292
Ser Thr Tyr Arg Glu Ile Gly Arg Arg Leu Lys Phe Trp Asn Glu Thr Asp Pro Glu    84

TTC GTC ATT GAC CAC ATG GAC GCA AAC AAG GCA GGG CGC TAT CAG TGC CAA TAT AGG   349
Phe Val Ile Asp His Met Asp Ala Asn Lys Ala Gly Arg Tyr Gln Cys Gln Tyr Arg   103

ATA GGG CAC TAC AGA TTC CGG TAC AGT GAC ACC CTG GAG CTG GTA GTG ACA GGC TTG   406
Ile Gly His Tyr Arg Phe Arg Tyr Ser Asp Thr Leu Glu Leu Val Val Thr Gly Leu   122

TAT GGC AAA CCC TTC CTC TCT GCA GAT CGG GGT CTG GTG TTG ATG CCA GGA GAG AAT   463
Tyr Gly Lys Pro Phe Leu Ser Ala Asp Arg Gly Leu Val Leu Met Pro Gly Glu Asn   141

ATT TCC CTC ACG TGC AGC TCA GCA CAC ATC CCA TTT GAT AGA TTT TCA CTG GCC AAG   520
Ile Ser Leu Thr Cys Ser Ser Ala His Ile Pro Phe Asp Arg Phe Ser Leu Ala Lys   160

GAG GGA GAA CTT TCT CTG CCA CAG CAC CAA AGT GGG GAA CAC CCG GCC AAC TTC TCT   577
Glu Gly Glu Leu Ser Leu Pro Gln His Gln Ser Gly Glu His Pro Ala Asn Phe Ser   179

TTG GGT CCT GTG GAC CTC AAT GTC TCA GGG ATC TAC AGG TGC TAC GGT TGG TAC AAC   634
Leu Gly Pro Val Asp Leu Asn Val Ser Gly Ile Tyr Arg Cys Tyr Gly Trp Tyr Asn   198

AGG AGC CCC TAC CTG TGG TCC TTC CCC AGT AAT GCC TTG GAG CTT GTG GTC ACA GAC   691
Arg Ser Pro Tyr Leu Trp Ser Phe Pro Ser Asn Ala Leu Glu Leu Val Val Thr Asp   217

TCC ATC CAC CAA GAT TAC ACG ACG CAG AAC TTG ATC CGC ATG GCC GTG GCA GGA CTG   748
Ser Ile His Gln Asp Tyr Thr Thr Gln Asn Leu Ile Arg Met Ala Val Ala Gly Leu   236

GTC CTC GTG GCT CTC TTG GCC ATA CTG GTT GAA AAT TGG CAC AGC CAT ACG GCA CTG   805
Val Leu Val Ala Leu Leu Ala Ile Leu Val Glu Asn Trp His Ser His Thr Ala Leu   255

AAC AAG GAA GCC TCG GCA GAT GTG GCT GAA CCG AGC TGG AGC CAA CAG ATG TGT CAG   862
Asn Lys Glu Ala Ser Ala Asp Val Ala Glu Pro Ser Trp Ser Gln Gln Met Cys Gln   274

CCA GGA TTG ACC TTT GCA CGA ACA CCA AGT GTC TGC AAG TAAACACCTG GAGGTGAAGG    920
Pro Gly Leu Thr Phe Ala Arg Thr Pro Ser Val Cys Lys                           287

CAGAGAGGAG CCAGGACTGT GGAGTCCGAC AAAGCTACTT GAAGGACACA AGAGAGAAAA GCTCACTAAG   990
AAGCTTGAAT CTACTTTTTT TTTTTTTTGA GACAGAGTCT GGCTCTGTCA CCCAGGCTGA AGTGCAGTGG 1060
AGCAATCTCG GCTCATTGAA CCTCTTGGGT TCAAGTGATT CTTGTGCCTC AGCCTCCCAA GTAGCTGGAA 1130
TTACAGGCAC ATACCACTGC ACCCAGCTAA TTTTTGTATT TTTAGTAGAG ATGGGGTTTC ACTGTGTTGG 1210
CCAGGCTGGT CTCGAACTCC TGGACCTCAG GTGATCCACC CACCTTGGCC TCCCAAAGTG CTGAGATTAT 1270
AGGCATGAGC CACCACGCCT GGCCAGATGC ATGTTCAAAC CAATCAAATG GTGTTTTCTT ATGCAGGACT 1340
GATCGATTTG CACCCACCTT TCTGCACATA AGTTATGGTT TTCCATCTTA TCTGTCTTCT GATTTTTTAT 1410
ATCCTGTTTA ATTTCTTCCT TCATTGTTCT TCTCTTTTTT TATTTATTTT ATTTATTTTT ATTTTTATTT 1480
TTATTTGAGA CAGAGTCTCA CTCTGTTGCC CAGGAGGCGG AGGTTGCAGT GAACCAAGAG ATGGCGCCAG 1550
TGCACTCCAC CCTGGGTGAC AGAGAGACTC TTTCTTTTTA AAAAAAAAAA AAAAAAAAA A           1611
```

FIGURE 2

ALIGNMENT SCORES FOR THE Ig FcR SUPERFAMILY

ALIGN SCORES

| SEQUENCE | IgA FcR$_1$ | IgA FcR$_2$ | IgG FcRI$_1$ | IgG FcRI$_2$ | IgG FcRII$_1$ | IgG FcRII$_2$ | IgG FcRIII$_1$ | IgG FcRIII$_2$ | IgE FcR$_1$ | IgE FcR$_2$ |
|---|---|---|---|---|---|---|---|---|---|---|
| IgAFcR$_1$ | - | 7.0 | 3.4 | 4.1 | 4.5 | 5.5 | 4.6 | 3.6 | 2.4 | 3.1 |
| IgAFcR$_2$ | 23.2 | - | 4.8 | 5.2 | 5.1 | 4.2 | 4.0 | 3.5 | 3.6 | 2.6 |
| IgGFcRI$_1$ | 22.4 | 24.7 | - | 4.8 | 15.9 | 5.2 | 14.6 | 4.6 | 15.3 | 3.2 |
| IgGFcRI$_2$ | 22.8 | 21.7 | 25.9 | - | 4.9 | 4.2 | 5.3 | 3.1 | 5.3 | 4.6 |
| IgGFcRII$_1$ | 24.1 | 25.3 | 49.4 | 26.5 | - | 6.0 | 17.2 | 5.6 | 13.0 | 3.4 |
| IgGFcRII$_2$ | 20.0 | 28.2 | 28.2 | 18.8 | 24.1 | - | 4.7 | 17.1 | 3.9 | 13.7 |
| IgGFcRIII$_1$ | 28.2 | 21.2 | 49.4 | 28.2 | 55.4 | 21.2 | - | 4.5 | 12.3 | 3.1 |
| IgGFcRIII$_2$ | 18.2 | 20.5 | 27.1 | 18.2 | 25.3 | 45.9 | 22.4 | - | 4.3 | 13.1 |
| IgEFcR$_1$ | 17.6 | 24.7 | 38.8 | 27.1 | 43.4 | 23.5 | 43.5 | 25.9 | - | 3.3 |
| IgEFcR$_2$ | 19.6 | 25.0 | 22.4 | 20.7 | 24.1 | 36.6 | 25.9 | 42.0 | 28.2 | - |

PERCENT IDENTITY

Figure 4

IgA-Rosette Formation by FcαR-transfected COS Cells

Inhibition of My 43 binding to PMA-induced U937 cells by supernatants from transfected COS cells

Characterization of recombinant soluble FcαR by SDS-PAGE/autoradiography

A,B = pDC303 Supernatant

C,D = pSol IgAR(−) Supernatant

E,F = pSol IgAR(+) Supernatant

DNA ENCODING IGA FC RECEPTORS

DESCRIPTION

1. Technical Field

The present invention relates generally to cell surface receptors, and more specifically, to IgA Fc receptors.

2. Background of the Invention

IgA is the predominant immunoglobulin isotype found in external secretions, including tears, saliva, colostrum and milk, respiratory, gastrointestinal, and genito-urinary secretions. In fact, although IgA is not found in high levels in the blood, its daily production exceeds production of all other isotypes. Secretory IgA production and secretion may be stimulated when an antigen is ingested or inhaled. The antigen penetrates mucosal epithelium and sensitizes, via T cells, antigen-specific B cells. The sensitized B cells then move out of the local site and migrate (via the thoracic duct) to the general circulation, eventually homing to distant mucosal sites and differentiating in the process. Thus, antigen encountered at one site stimulates dissemination of an IgA-mediated response to distal sites. The end result is prevention of infectious disease contracted through the large area of mucosal surfaces and inhibition of uptake of potentially allergenic environmental substances.

Serum IgA is predominantly monomeric, consisting of two H and two L chains (i.e., two binding sites) (see J. Mestecky and J. R. McGhee, "Immunoglobulin A (IgA):Molecular and Cellular Interactions Involved in IgA Biosynthesis and Immune Response," *Advances in Immunology* 40:153-245). In contrast, mucosal secretions contain polymeric forms of IgA (largely dimers) with attached J chains and secretory component (SC). Polymerization is initiated through incorporation of the J chain within the B cell. Following secretion from the B cell, polymeric IgA is taken up by SC on the basolateral surface of mucosal epithelial cells, endocytosed, transported through the epithelial cell, and released into the mucosal lumen with SC attached. The SC functions not only in transporting IgA to secretions, but also protects IgA from proteolytic cleavage.

IgA fulfills a critical protective role against the constant environmental insults encountered at mucosal surfaces (B. J. Underdown and J. M. Schiff, Ann. Rev. *Immunol.* 4:489-417, 1986). Although the mechanism of protection is not completely defined, the IgA-mediated mucosal immune response may be at least partially manifested through binding of IgA-coated targets to Fc receptors on effector cells. In particular, monocytes, macrophages, neutrophils, and myeloid cell lines have been shown to express cell surface IgA Fc receptors (FcαR) (see M. W. Fanger et al., Proc. Natl. Acad. Sci. 77:3640-44, 1980; J. Gauldie et al., Molec. Immunol. 20:1029-37, 1983; C. R. Maliszewski et al., J. Immunol. 135:3878-81, 1985; and A. Chevalier et al., J. Immunol. 142:2244-49, 1989), which mediate effector functions such as phagocytosis (see M. W. Fanger et al., Molec. Immunol. 20:1019-27, 1983; L. Shen et al., Molec. Immunol. 23:611-18, 1986), antibody-dependent cell cytotoxicity (L. Shen and M. W. Fanger, Molec. Immunol. 59:75-81, 1981), and inflammatory mediator release (N. R. Ferreri et al., J. immunol. 136:4188-93, 1986). Other studies indicate that the human myeloid cell FcαR is heterogeneously charged, ~60-kD molecule which, upon deglycosylation, can be resolved to two protein cores of 32- and 36-kD (M. Albrechtson et al., Immunology 64:201-205, 1988; and R. C. Monteiro et al., J. Exp. Med. 171:597-613, 1990).

The present invention provides membrane bound and soluble forms of a mammalian Fc receptor for IgA, and further provides other related advantages.

SUMMARY OF THE INVENTION

The present invention provides isolated DNA sequences encoding mammalian IgA Fc receptor proteins and, in particular, human IgA Fc receptor proteins. Within one embodiment the DNA sequence comprises the sequence of nucleotides 1 to 900, depicted in FIG. 2. Within another aspect of the present invention, a DNA sequence is provided which encodes a soluble mammalian IgA Fc receptor. Within one embodiment, the DNA sequence comprises the sequence of nucleotides 40 to 720, depicted in FIG. 2. Within yet another embodiment, the DNA sequence is selected from the group consisting of (a) cDNA clones having a nucleotide sequence derived from the coding region of a native mammalian IgA Fc receptor gene; (b) DNA sequences capable of hybridization to the clones of (a) under moderately stringent conditions and which encode biologically active IgA Fc receptor protein; and (c) DNA sequences which are degenerate as a result of the genetic code to the DNA sequences defined in (a) and (b) and which encode biologically active IgA Fc receptor protein. Also provided by the present invention are recombinant expression vectors and host cells which contain these DNA sequences.

The present invention also provides isolated mammalian IgA Fc receptor proteins and, in particular, human IgA Fc receptor proteins. Within one embodiment, the isolated IgA Fc receptor proteins comprise the sequence of amino acids as shown in FIG. 2, from glutamine, amino acid number 1, to lysine, amino acid number 266. Within another aspect of the present invention, an isolated soluble mammalian IgA Fc receptor is provided. Within one embodiment, the isolated soluble IgA Fc receptor comprises the sequence of amino acids, as shown in FIG. 2, from glutamine, amino acid number 1, to asparagine, amino acid number 206.

Within yet another aspect of the present invention, methods are provided for preparing an IgA Fc receptor or soluble IgA Fc receptor, comprising culturing a suitable host cell under conditions promoting expression.

The present invention also provides a composition comprising an effective amount of a soluble IgA Fc receptor, and a suitable diluent or carrier.

These and other aspects of the present invention will become evident upon reference to the following detailed description and attached drawings.

BRIEF DESCRIPTION OF THE DRAWINGS

FIG. 2 depicts human FcαR nucleotide and predicted amino acid sequences. Nucleotides are numbered beginning at the 5' terminus and amino acids are numbered beginning with the predicted amino terminus (Gln 22) of mature FcαR, which is marked with an arrowhead.

Cysteine residues are boxed and potential N-linked glycosylation sites are marked with an asterisk.

Figure 3:
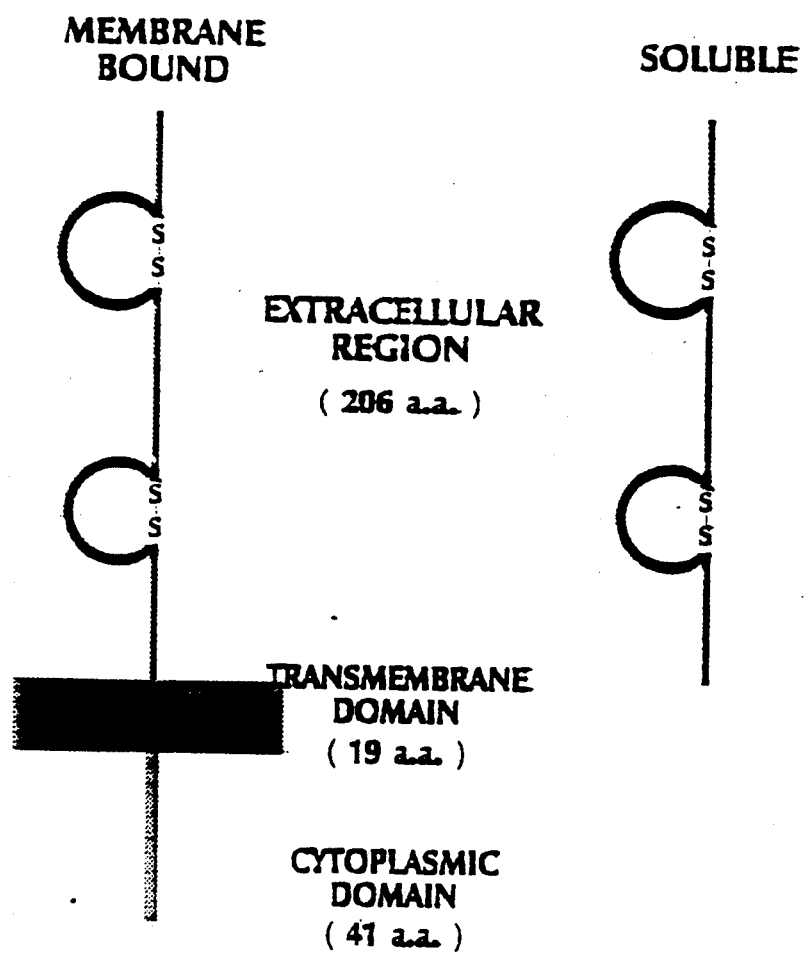

FIG. 3 illustrates the predicted structure of both membrane bound and soluble forms of a representative IgA Fc receptor.

FIG. 4 depicts alignment scores and percent sequence identity for the Ig Fc receptor family.

Figure 5:
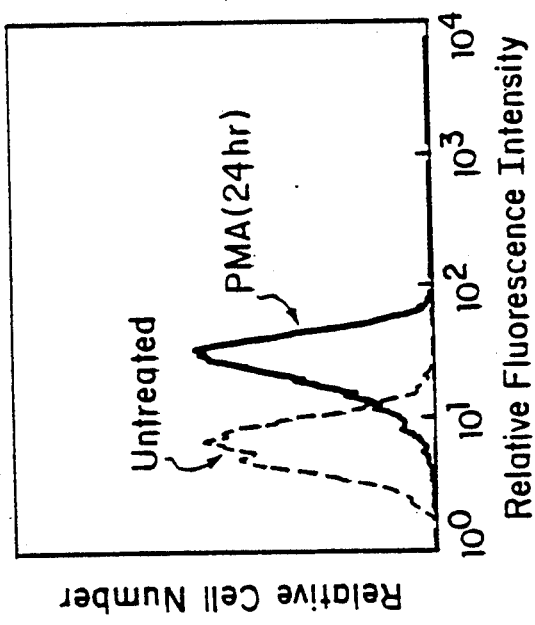

FIG. 5 illustrates IgA Fc receptor expression for untreated and PMA-treated U-937 cells.

Figure 6:
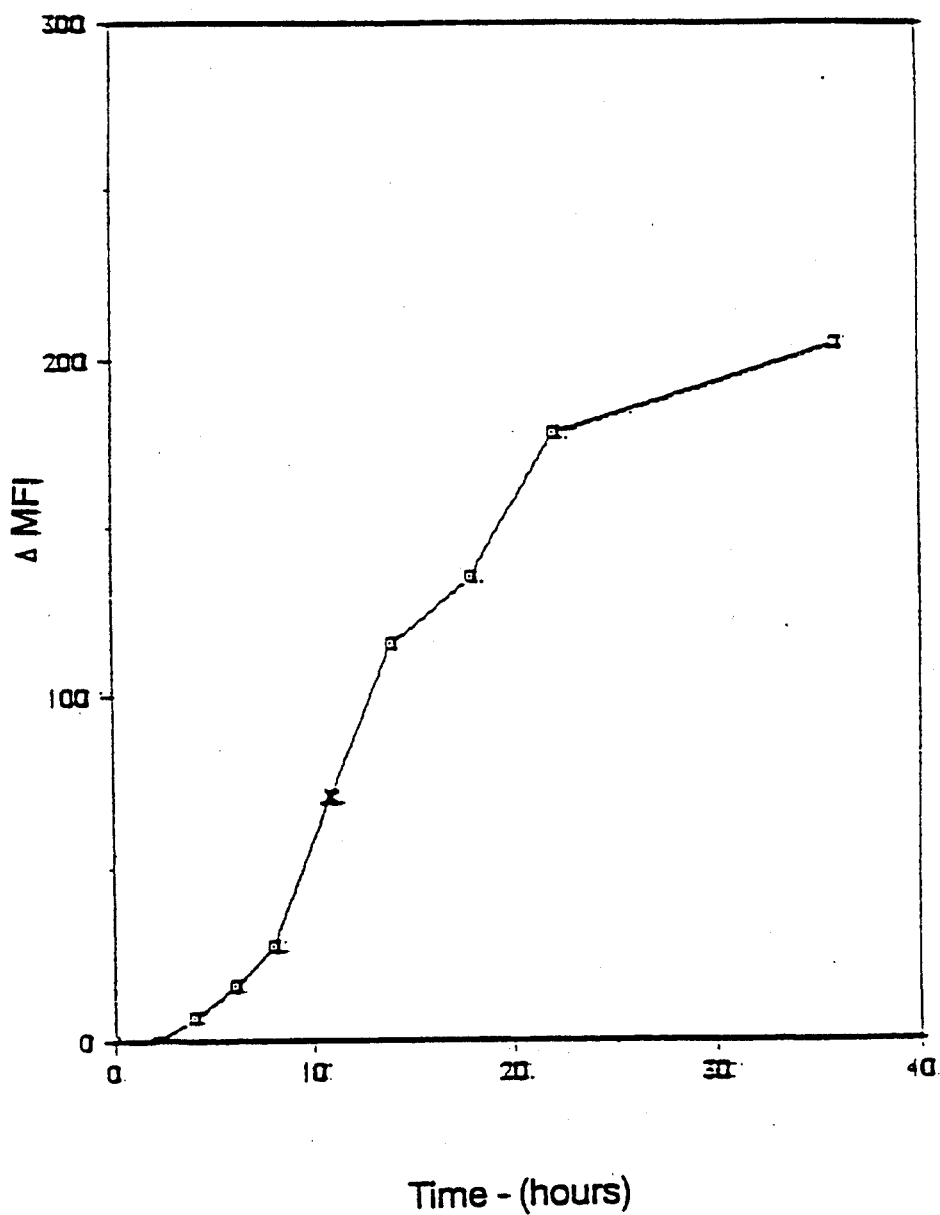

FIG. 6 illustrates IgA Fc receptor expression over time after PMA treatment of U-937 cells. "Δ MFI" or the change in Mean Fluorescence Intensity is determined by the following formula: Δ MFI=MFI (at time X)-MFI (at time 0). MFI at time 0=80.

Figure 7:
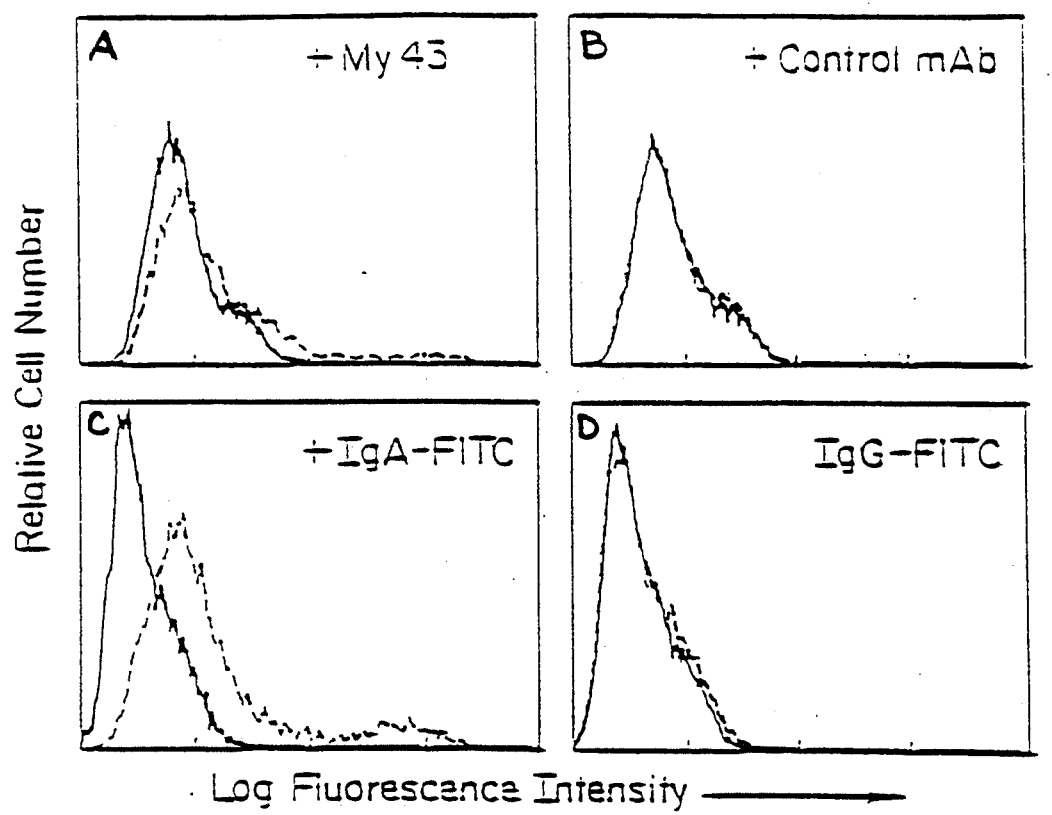

FIG. 7 illustrates the expression of FcαR cDNA in transfected cells. FIGS. 7A–7B illustrate the specificity of My43 for the FcαR. Control plasmid (solid line) and FcαR plasmid (dashed line) transfected COS cells were stained with either My43 or a murine IgM isotype control and analyzed by flow cytometry. FIGS. 7C–7C demonstrate the specificity of the FcαR for IgA. Control and FcαR-transfected COS cells were stained with human IgA-FITC or human IgG-FITC and analyzed by flow cytometry.

Figures 8A, 8B, 8C:
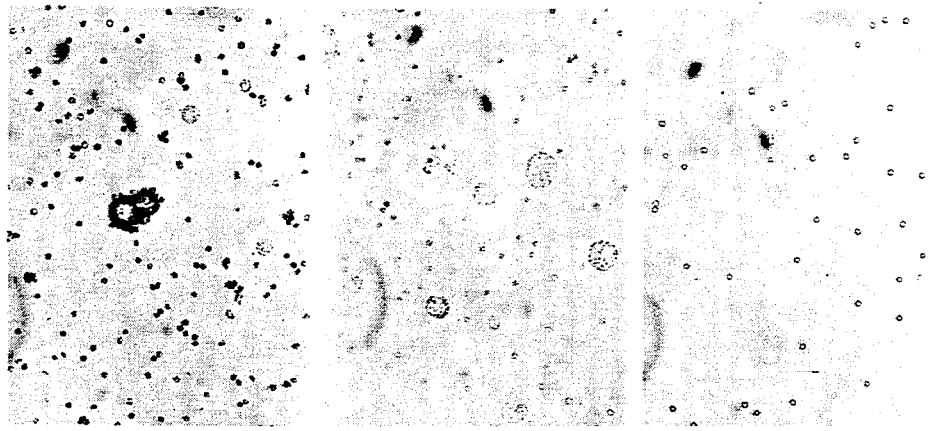

FIG. 8 illustrates specific rosette formation by FcαR transfected COS cells. COS cells were transfected with FcαR plasmid (FIGS. 8A, 8B) and with pDC303 (FIG 8C) and incubated with human IgA- (FIGS. 8A, 8C) or human IgG1- (FIG. 8B) coated ox red blood cells (ORBC) and microscopically analyzed for rosette formation.

Figure 9:

FIG. 9 depicts a northern blot analysis of FcαR transcripts in poly A+ mRNA from: 1) 12-hour PMA-stimulated U937;2) unstimulated U937; 3)neutrophils; 4) peripheral blood monocytes; 5) PWM-stimulated tonsillar B cells; 6) PMA/inomycin treated tonsillar B cells; 7) unstimulated tonsillar B cells; 8) PHA stimulated tonsillar T cells; 9) unstimulated tonsillar T cells; and 10) total RNA from human dermal fibroblasts.

Figure 10:
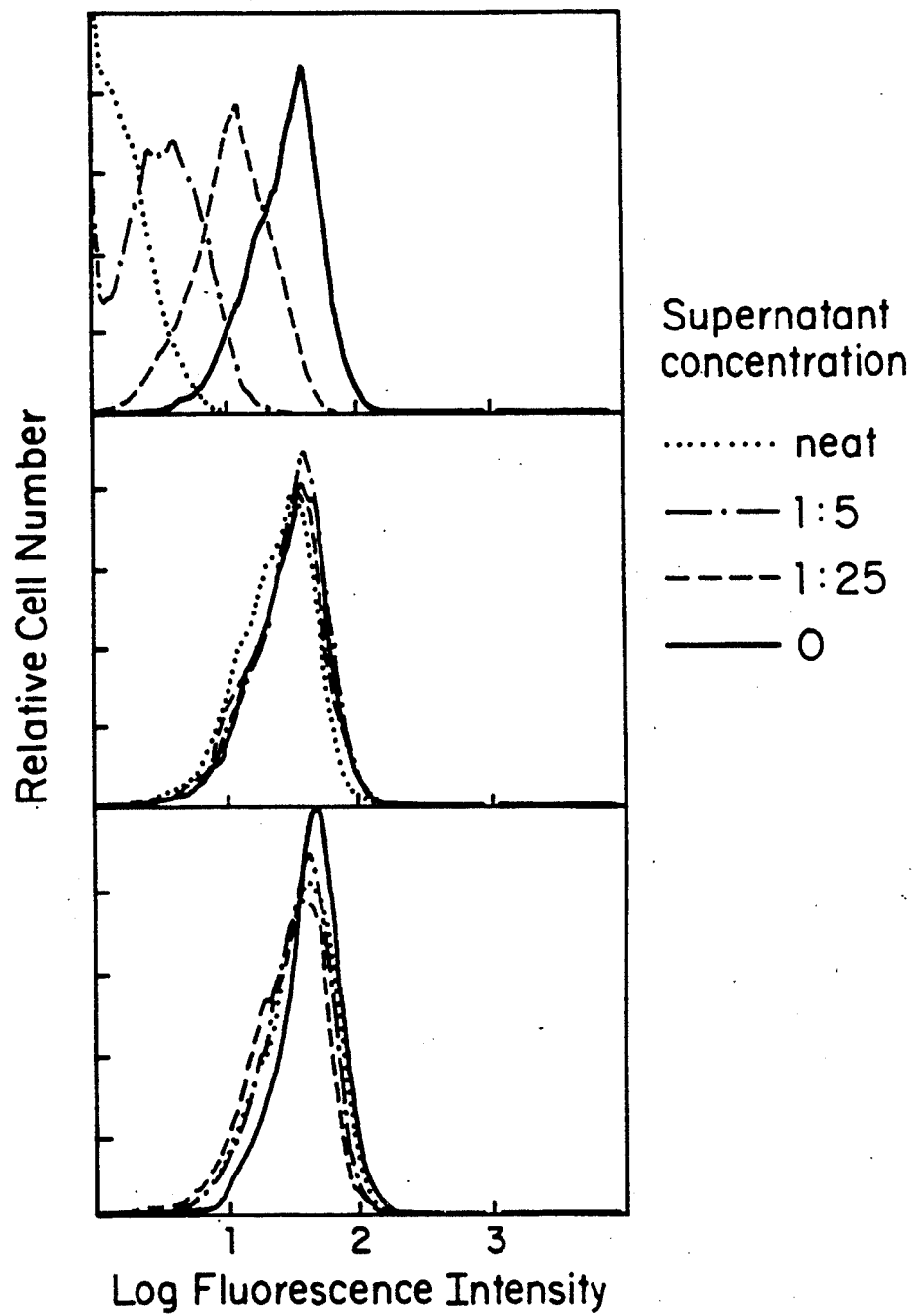

FIG. 10 illustrates the inhibition of My43 binding to PMA-induced U937 cells by supernatants of COS cells transfected with pSolFcαR.

Figure 11:
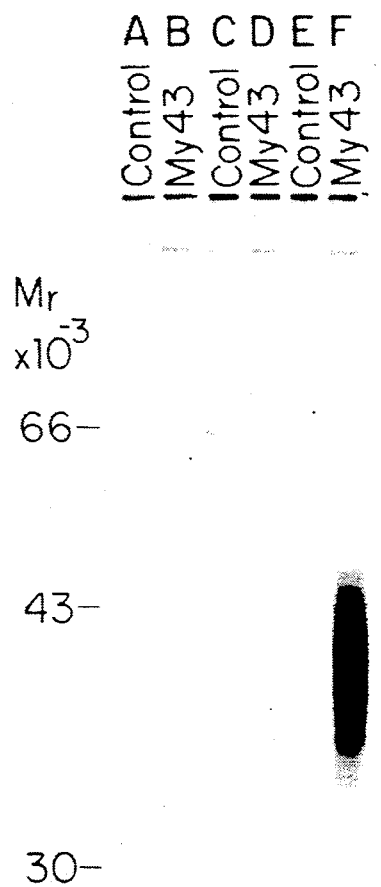

FIG. 11 illustrates the binding of My43 to recombinant soluble FcαR by SDS-PAGE/autoradiography.

DETAILED DESCRIPTION OF THE INVENTION

Definitions

Prior to setting forth the invention, it may be helpful to an understanding thereof to set forth definitions of certain terms to be used hereinafter.

"Mammalian IgA Fc Receptor" (FcαR) is a receptor protein which binds the immunoglobulin IgA. In its native configuration, FcαR exists as a membrane-bound protein, consisting of an extracellular region which binds to IgA, a hydrophobic transmembrane region which immobilizes the protein within the cell's lipid bilayer, and an intracellular region. Within the context of the present invention, FcαR includes both the membrane-bound forms of FcαR in addition to the soluble forms as defined below. Additionally, FcαR analogs which are biologically active and which are substantially similar to the sequences disclosed in FIG. 2, in that they are capable of binding FcαR or transducing a biological signal initiated by an IgA molecule binding to a cell, or cross reacting with anti- FcαR antibodies raised against FcαR from natural (i.e., non-recombinant) sources, are considered to be within the scope of the present invention. For purposes of the present invention, mammalian FcαR includes among others, human, murine, canine, feline, bovine, ovine, equine, and porcine FcαR.

"Soluble IgA Fc Receptor", "Sol FcαR", or "sFcαR" refers to a protein which has an amino acid sequence corresponding to the extracellular region of membrane bound FcαR. The extracellular region of human FcαR corresponds to amino acids 1 to 266 in FIG. 2, or the amino acid sequences discussed in Example 5, sFcαR analogs which are biologically active and which are substantially similar to the sequence of the extracellular region disclosed within FIG. 2, are also considered to be within the scope of the present invention. Substantially similar soluble FcαRs include polypeptides which vary from these sequences by one or more substitutions, deletions, or additions, and which retain the ability to bind IgA or inhibit IgA signal transduction activity via cell surface bound FcαRs proteins. Analogous deletions may be made to murine FcαRs. Inhibition of IgA signal transduction activity may be determined by transfecting cells with recombinant FcαR DNAs to obtain recombinant receptor expression. The cells are then contacted with IgA and the resulting metabolic effects examined. If an effect results which is attributable to the action of the ligand, then the recombinant receptor has signal transduction activity. Examplary procedures for determining whether a polypeptide has signal transduction activity are disclosed by Idzerda et al., J. Exp. Med. 171:861 (1990); Curtis et al., Proc. Natl. Acad. Sci. USA 86:3045 (1989); Prywes et al., EMBO J. 5:2179 (1986) and Chou et al., J. Biol. Chem. 262:1842 (1987). Alternatively, primary cells or cell lines which express an endogenous FcαR and have a detectable biological response to IgA may also be utilized. Signal transduction activity may also be measured by functions which are attributable to IgA-IgA receptor interactions, for example, phagocytosis, ADCC, or soluble-mediated release functions.

"Biologically active" as used within the present invention means that a particular molecule is capable of binding detectable quantities of IgA. Various assays, as discussed below, may be utilized to determine IgA binding, for example, the inhibition of IgA rosette formation (Example 6B).

"DNA sequence" refers to a DNA molecule, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where the same do not interfere with manipulation or expression of the coding regions.

"Recombinant expression vector" refers to a replicable DNA construct used either to amplify or to express DNA which encodes RcαR or sFcαR. This construct comprises an assembly of (1) a genetic element or elements having a regulator role in gene expression, for example, promoters or enhancers, (2) a structural or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

Proteins and Analogs

Figure 1:
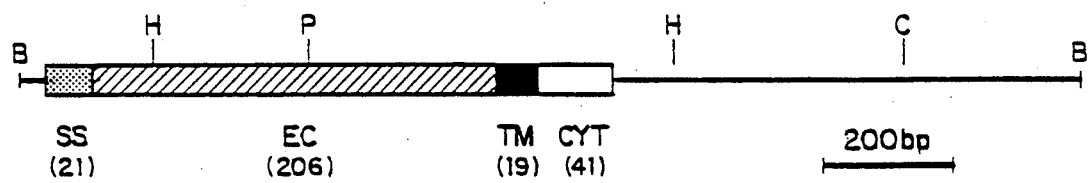
FIG. 1 is a restriction map which schematically illustrates human FcαR cDNA. Restriction sites are indicated for the enzymes Bgl II (B), Cla I (C), Hind III (H), and Pst I (P). The boxed coding region depicts the predicted domain structure, including signal sequence (SS), extracellular (EC), transmembrane (TM), and cytoplasmic (CYT) domains.

As noted above, the present invention provides an isolated DNA sequence encoding a mammalian IgA Fc receptor (FcαR). FIG. 1 is a restriction map illustrating a cDNA clone which contains the sequence encoding a human FcαR. The cDNA clone is composed of a 39 bp 5' untranslated region, an 861 bp open reading frame, and a 711 bp 3' untranslated region, terminating in a poly-A tact. The open reading frame (the boxed region) is composed of a signal sequence (SS), extracellular region (EC), transmembrane region (TM), and cytoplasmic domain (CYT). The open reading frame encodes a protein of 287 amino acids, the first 21 amino acids of which exhibit characteristics of a hydrophobic signal sequence. Upon expression, the signal sequence is cleaved, resulting in a mature receptor which begins at Gln 22. The predicted molecular weight of the mature receptor is approximately 29,900 daltons.

The 206 amino acid extracellular domain includes six potential sites for N-linked glycosylation, a feature which along with O-glycosylation could account for the significantly higher molecular weight observed in native FcαR. The four cysteines in the extracellular region as well as specific residues in proximity of the cysteines are identical to residues at analogous sites in other members of the Fc receptor family. In addition, significant ALIGN scores were obtained when the extracellular FcαR sequence was compared with the other Fc receptor sequences and other members of the immunoglobulin gene superfamily, suggesting that FcαR should also be included in this group of related proteins (see FIG. 4). Structurally, this would imply that the extracellular region of FcαR is composed of two domains defined by intrachain disulfide bonds connecting Cys 28 to Cys 79, and Cys 125 to Cys 172 (see FIG. 3).

The extracellular region is followed by a 19 residue stretch of hydrophobic amino acids corresponding to the transmembrane domain (FIGS. 1, 2, and 3) and a 41-residue cytoplasmic domain. However, two features of the putative transmembrane region are atypical of "protein-anchored" transmembrane proteins, namely the presence of a charged residue (Arg 230) and the lack of a cluster of basic residues immediately following the hydrophobic stretch. Nevertheless, at least two alternative modes of attachment are possible, either through a glycosyl-phosphatidyl inositol (GPI) linkage or by association with another protein.

Also provided within the present invention are soluble forms of the IgA Fc receptor (SfcαR). As is illustrated in FIG. 3 within one embodiment, the sFcαR is composed of only the 206 amino acid extracellular region, with the transmembrane and cytoplasmic domains deleted. As will be discussed below, the sFcαR may be administered therapeutically as a vaccine adjuvant, or to inhibit IgA-mediated phagocytosis.

As discussed above, the present invention provides mammalian IgA Fc receptor and soluble mammalian IgA Fc receptor proteins substantially free of contaminating endogenous materials and, optionally without associated native-pattern glycosylation. Derivatives of FcαR within the scope of the invention also include various structural forms of the primary protein which retain biological activity. Due to the presence of ionizable amino and carboxyl groups, for example, an FcαR protein may be in the form of acidic or basic salts, or in neutral form. Individual amino acid residues may also be modified by oxidation or reduction.

Also provided by the present invention are FcαR and sFcαR like proteins which are biologically active, and which have substantial similarity to the FcαR or sFcαR sequences disclosed in FIG. 2. As will be evident to one of ordinary skill in the art, various substitutions, deletions, or additions may be made to the amino acid or DNA sequences, the net effect of which is to retain biological activity of the FcαR protein. Within one aspect of the present invention, a DNA sequence is deemed to be "substantially similar" to the specific DNA sequences disclosed herein if: (a) the DNA sequence is derived from the coding region of a native mammalian FcαR gene; (b) the DNA sequence is capable of hybridization to DNA sequences of the present invention under moderately stringent conditions and encode biologically active FcαR molecules; or (c) DNA sequences are degenerate as a result of the genetic code to the DNA sequences defined in (a) or (b) and encodes biologically active FcαR molecules. Furthermore, like most mammalian genes, mammalian FcαR receptors are presumably encoded by multi-exon genes. Alternative mRNA constructs which may be attributed to different mRNA splicing events following transcription, and which share large regions of identity with the cDNAs claimed herein, are considered to be within the scope of the present invention. Substantially similar proteins will generally be greater than about 30% similar to the corresponding sequence of the native FcαR. More preferably, the substantially similar proteins will be greater than about 80% similar to the corresponding sequence of the native FcαR. Percent similarity may be determined, for example, by comparing sequence information using the GAP computer program, version 6.0, available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math. 2:482, 1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (Nucl. Acids Res. 14:6745, 1986), as described by Schwartz and Dayhoff (ed., Atlas of Protein Sequence and Structure, National Biomedical Research Foundation, pp. 353-358, 1979); (2) a penalty of 3.0 for each gap and an additional 0.10 penalty for each symbol in each gap; and (3) no penalty for end gaps.

The primary amino acid structure may also be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups of FcαR amino acid side chains or at the N- or C-termini. Other derivatives of FcαR within the scope of this invention include covalent or aggregative conjugates of FcαR or its fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader). FcαR protein fusions may also comprise peptides added to facilitate purification or identification of FcαR (e.g., poly-His). More specifically, a fusion construct such as human FcαR (1-266) (His)$_n$ or sFcαR (1-206) (His)$_n$ may be constructed in order to allow purification of the protein via the poly-His residue, for example, on a NTA nickel-chelating column. The amino acid sequence of FcαR receptor may also be linked to the peptide Asp-Tyr-Lys-Asp-Asp-Asp-Asp-Lys (DYKDDDDK) (Hopp et al., Bio/Technology 6:1204, 1988.) The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradiation in *E. coli*. A specific example of such a peptide is soluble human FcαR (1-206) Asp Tyr Lys Asp Asp Asp Asp Lys.

The present invention also includes FcαR proteins with or without associated native-pattern glycosylation. FcαR expressed in yeast or mammalian expression systems, e.g., COS-7 cells, may be similar or significantly different in molecular weight and glycosylation pattern than the native molecules, depending upon the expression system. Expression of FcαR DNAs in bacteria such as *E. coli* provides non-glycosylated molecules. Functional mutant analogs of mammalian FcαR having inactivated N-glycosylation sites may be produced by oligonucleotide synthesis and ligation or by site-specific mutagenesis techniques. These analog proteins may be produced in a homogeneous, reduced-carbohydrate form in good yield using yeast expression systems. N-glycosylation sites in eukaryotic proteins are generally characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$.

Proteins which are biologically active and substantially similar to FcαR proteins may also be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively, i.e., the most preferred substitute amino acids are those having physicochemical characteristics resembling those of the residue to be replaced. When a substitution, deletion, or insertion strategy is adopted, the potential effect of the deletion or insertion on biological activity should be considered. Various assays such as the inhibition of IgA rosette formation (Example 6B), as discussed below, may be utilized to assess the affect of such modifications upon biological activity.

As discussed above, subunits of FcαR may be constructed by deleting terminal or internal residues or sequences. Particularly preferred subunits include those in which the transmembrane region and intracellular domain of FcαR are deleted or substituted with hydrophilic residues to facilitate secretion of the receptor into the cell culture medium. The resulting protein is a soluble FcαR molecule which may retain its ability to bind FcαR.

Mutations in nucleotide sequences constructed for expression of proteins which are substantially similar to FcαRs must preserve the reading frame phase of the coding sequences. Furthermore, the mutations will preferably not create complementary regions that could hybridize to produce secondary mRNA structures, such as loops or hairpins, which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed FcαR mutants screened for the biological activity.

Not all mutations in the nucleotide sequence which encodes FcαR will be expressed in the final product. For example, nucleotide substitutions may be made to enhance expression by avoiding secondary structure loops in the transcribed mRNA, or to provide codons that are more readily translated by the selected host, e.g., the well-known, *E. coli* preference codons for *E. coli* expression.

Mutantions may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures may be employed to provide an altered gene having particular codons altered according to the substitution, deletion, or insertion required. Exemplary methods of making the alterations set forth above are disclosed by Walder et al. (gene 42:133, 1986); Bauer et al. (gene 37:73, 1985); Craik, Bio Techniques, January 1985, 12–19); Smith et al. (genetic Engineering: Principles and Methods, Plenum Press, 1981); Sambrook et al. (Molecular cloning: A Laboratory Manual, 2d Ed., Cold Spring Harbor Laboratory Press, 1989); and U.S. Pat. Nos. 4,518,584 and 4,737,462, which are incorporated by reference herein.

FcαR analogs may be used as therapeutic reagents, immunogens, reagents in receptor-based immunoassays, or as binding agents for affinity purification procedures of IgA or other binding ligands such as an anti-IgA receptor monoclonal. FcαR derivatives may also be obtained by utilizing crosslinking agents, such as M-maleimidobenzoyl succinimide ester and N-hydroxysuccinimide, at cysteine and lysine residues. FcαR proteins may also be covalently bound through reactive side groups to various insoluble substrates, such as cyanogen bromine-activated, bisoxirane-activated, carbonyldiimidazole-activated, or tosyl-activated, agarose structures, or by adsorbing to polyolefin surfaces (with or without glutaraldehyde cross-linking). Once bound to a substrate, FcαR may be used to selectively bind (for purposes of assay or purification) anti-FcαR antibodies or IgA.

Expression of Redcombinant FcαR

The present invention provides recombinant expression vectors which include synthetic or cDNA-derived DNA fragments encoding mammalian FcαR or substantially similar proteins which are operably linked to suitable transciptional or translational regulator elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated. DNA regions are operable linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame.

DNA sequences encoding FcαR receptors which are to be expressed in a microorganism will preferably contain no introns that could prematurely terminate transcription of DNA into mRNA. However, premature termination of transcription may be desirable, for example, where it would result in mutants having advantageous C-terminal truncations, for example, deletion of a transmembrane region to yield a soluble receptor not bound to the cell membrane. Due to code degeneracy, there may be considerable variation in nucleotide sequences encoding the same amino acid sequence. Other embodiments include sequences capable of hybridizing to the sequence of FIG. 2 under moderately stringent conditions (50° C., 2 x SSC) and other sequences hybridizing or degenerate to those described above, which encode biologically active FcαR receptor polypeptides.

DNA which codes for soluble FcαR proteins may be isolated using the cloning techniques described in the examples or may be made by constructing cDNAs which encode only the extracellular domain of FcαR receptor (devoid of a transmembrane region) using well known methods of mutagenesis. cDNAs which encode sFCαR may also be constructed, for example, by truncating a cDNA encoding the full length FcαR receptor 5' of the transmembrane region, ligating schematic synthetic oligonueleotides to regenerate truncated portions of the extracellular domain, if necessary, and providing a stop codon to terminate transcription, DNA sequences encoding the soluble FcαR receptor proteins may be assembled from cDNA fragments and short oligonucleotide linkers, or from a series of oligonucleotides, to provide a synthetic gene which is capable of being expressed in a recombinant transcriptional unit. Such DNA sequences are preferably provided in the form of an open reading frame uninterrupted by internal nontranslated sequences, or introns, which are typically present in eukaryotic genes. Genomic DNA containing the relevant sequences could also be used. Sequences of nontranslated DNA may be present 5' or 3' from the open reading frame, where the same do not interfere with manipulation or expression of the coding regions.

Transformed host cells are cells which have been transformed or transfected with FcαR vectors constructed using recombinant DNA techniques. Expressed FcαR will be deposited in the cell membrane or secreted into the culture supernatant, depending on the FcαR DNA selected. Suitable host cells for expression of mammalian FcαR include prokaryotes, yeast or higher eukaryotic cells under the control of appropriate promoters. Prokaryotes include gram negative or gram positive organisms, for example, E. coli or bacilli. Higher eukaryotic cells include established cell lines of mammalian origin as described below. Cell-free translation systems could also be employed to produce mammalian FcαR using RNAs derived from the DNA constructs of the present invention. Appropriate cloning and expression vectors for use with bacterial, fungal, yeast, and mammalian cellular hosts are described by Pouwels et al. (Cloning Vectors: A Laboratory Manual, Elsevier, New York, 1985), the relevant disclosure of which is hereby incorporated by reference.

Prokaryotic expression hosts may be used for expression of FcαRs that do not require extensive proteolytic and disulfide processing. Prokaryotic expression vectors generally comprise one or more phenotypic selectable markers, for example, genes encoding proteins conferring antibiotic resistance or supplying an autotrophic requirement, and an origin of replication recognized by the host to ensure amplification within the host. Suitable prokaryotic hosts for transformation include E. coli, Bacillus subtillis, Salmonella typhimurium, and various species within the genera Pseudomonas, Streptomyces, and Staphylococcus, although others may also be employed as a matter of choice.

Expression vectors for bacteria may comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis.). These pBR322 "backbone" sections are combined with an appropriate promoter and the structural sequence to be expressed. E. coli is typically transformed using derivatives of pBR322, a plasmid derived from an E. coli species (bolivar et al., Gene 2:95 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., Nature 275:615, 1978; and Goeddel et al., Nature 281:544, 1979), the tryptophan (trp) promoter system (Goeddel et al., Nucl. Acids Res. 8:4057, 1980; and EPA 36,776)

and tac promoter (Maniatis, Molecular Cloning: A Laboratory Manual, Cold Spring Harbor Laboratory, p. 412, 1982). A particularly useful bacterial expression system employs the phage λ $P_L$ promoter and c1857ts thermolabile repressor. Plasmid vectors available from the American Type Culture Collection which incorporate derivatives of the λ $P_L$ promoter include plasmid pHUB2, resident in *E. coli* stain JMB9 (ATCC 37092) and pPLc28, resident in *E. coli* RRa (ATCC 53082).

Recombinant FcαR proteins may also be expressed in yeast hosts, preferably from the Saccharomyces genus, such as *S. cerevisiae*. Yeast of other genera, such as Pichia or Kluyveromyces may also be employed. Yeast vectors will generally contain an origin of replication from the 2μ yeast plasmid or an autonomously replicating sequence (ARS), promoter, DNA encoding FcαR, sequences for polyadenylation and transcription termination and a selection gene. Preferably, yeast vectors will include an origin of replication and selectable marker permitting transformation of both yeast and *E. coli*, e.g., the ampicilin resistance gene of *E. coli* and *S. cerevisiae* trp1 gene, which provides a selection marker for amutant strain of yeast lacking the ability to grow in the absence of tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., J. Biol. Chem. 255:2073, 1980) or other glycolytic enzymes (Hess et al., J. Adv. Enzyme Reg. 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyrovate kinase, triosephosphate isomerase, phosphoglucose isomerase, and glucokinase. Suitable vectors and promoters for use in yeast expression are further described in Hitzeman, EPA 73,657.

Preferred yeast vectors may be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (J. Biol. Chem. 258:2674, 1982) and Beier et al. (Nature 300:724, 1982). The yeast α-factor leader, which directs secretion of heterologous proteins, may be inserted between the promoter and the structural gene to be expressed. See, e.g., Kurjan et al., Cell 30:933, 1982; and Bitter et al., Proc. Natl. Acad. Sci. USA 81:5330, 1984. The leader sequence may also be modified to contain, near its 3' end, one or more useful restriction sites to facilitate fusion of the leader sequence to foreign genes.

Suitable yeast transformation protocols are known to those of skill in the art; an exemplary technique is described by Hinnen et al., Proc. Natl. Acad. Sci. USA 75:1929, 1978, selecting for Trp+ transformants in a selective medium consisting of 0.67% yeast nitrogen base, 0.5% casamino acids, 2% glucose, 10 μg/ml adenine and 20 μg/ml uracil.

Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems may also be employed to express recombinant protein. Baculovirus systems for production of heterologous proteins in insect cells are reviewed by Luckow and Summers, Bio/Technology 6:47, 1988. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and later promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., Nature 273:113, 1978). Smaller or larger SV40 fragments may also be used, provided the approximately 250 bp sequence extending from the Hind III site toward the Bg II site located in the viral origin of replication is included. Further, mammalian genomic FcαR promoter, control and/or signal sequences may be utilized, provided such control sequences are compatible with the host cell chosen. Exemplary vectors may be constructed as disclosed by Okayama and Berg (Mol. Cell. Biol. 3:280, 1983).

A useful system for stable high level expression of mammalian receptor cDNAs in C127 murine mammary epithelial cells can be constructed substantially as described by Cosman et al. (Mol. Immunol. 23:935, 1986).

A particularly preferred eukaryotic vector for expression of FcαR DNA is disclosed below in Example 1. This vector, referred to as pDC303, was derived from the mammalian high expression vector pDC302 and contains regulatory sequences from SV40, adenovirus-2, and human cytomegalovirus.

Purification of FcαR

Isolated FcαR or substantially similar proteins may be prepared by culturing suitable host/vector systems to express the recombinant translation products of the DNAs of the present invention, and purifying FcαR protein from the culture media or cell extracts. Within the context of the present invention, "isolated" or "purified," as used to define the purity of FcαR protein or protein compositions, means that the protein or protein composition is substantially free of other proteins of natural or endogenous origin and contains less than about 1% by mass of protein contaminants due to the residual of production processes. Such compositions, however, may contain other proteins added as stabilizers, carriers, excipients or co-therapeutics. FcαR is isolated if it is detectable as a single protein band in a polyacrylamide gel by silver staining.

Within one embodiment, supernatants from systems which secrete recombinant protein into culture media are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise IgA, a lectin or antibody molecule bound to a suitable support. Alternatively, an anion exchange resin may be employed, for example, a matrix or substrate having pendant diethylaminoethyl (DEAE) groups. Suitable matrices include acrylamide, agarose, dextran, cellulose or other types commonly employed in protein purification. Alternatively, a cation exchange step may be employed. Suitable cation exchangers include various insoluble matrices comprising sulfopropyl or carboxymethyl groups. Sulfopropyl groups are particularly preferred.

Finally, one or more reversed-phase high performance liquid chromatography (RP-HPLC) steps employing hydrophobic RP-HPLC media, e.g., silica gel having pendant methyl or other aliphatic groups, may be employed to further purify an FcαR composition. Some or all of the foregoing purification steps, in various combinations, can also be employed to provide a homogeneous recombinant protein.

Recombinant protein produced in bacterial culture may usually be isolated by initial extraction from cell pellets, followed by one or more concentration, salting-out, aqueous ion exchange or size exclusion chromatography steps. Additionally, as discussed above, the recombinant protein may be purified by affinity chromatography. Finally, high performance liquid chromatography (HPLC) may be employed for final purification steps. Microbial cells employed in expression of recombinant FcαR may be disrupted by any convenient method, including freeze-thaw cycling, sonication, mechanical disruption, or through the use of cell lysing agents.

Fermentation of yeast which express FcαR as a secreted protein greatly simplifies purification. Secreted recombinant protein resulting from a large-scale fermentation may be purified by methods analogous to those disclosed by Urdal et al. (J. Chromatog. 296:171, 1984). This reference describes two sequential, reversed-phase HPLC steps for purification of recombinant human IL-2 on a preparative HPLC column. Alternatively, techniques such as affinity chromatography as discussed above, may be utilized to purify the FcαR.

Mammalian FcαR synthesized in recombinant culture is characterized by the presence of non-human cell components, including proteins, in amounts and of a character which depend upon the purification steps taken to recover the FcαR from culture. These components ordinarily will be of yeast, prokaryotic or non-human higher eukaryotic origin and preferably are present in innocuous contaminant quantities, on the order of less than about 1% by weight. Further, recombinant cell culture enables the production of FcαR free of proteins which may be normally associated with FcαR as it is found in nature in its species of origin, e.g., in cells, cell exudates or body fluids.

Administration of FcαR

For therapeutic use, purified sFcαR may be administered to a patient, for treatment in a manner appropriate to the indication. sFcαR may be administered by bolus injection, continuous infusion, sustained release from implants, or other suitable technique. Typically, a sFcαR therapeutic agent will be administered in the form of a composition comprising purified protein in conjunction with physiologically acceptable carriers, excipients or diluents. Such carriers will be nontoxic to recipients at the dosages and concentrations employed. Ordinarily, the preparation of such compositions entails combining the sFcαR with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, the product is formulated as a lyophilizate using appropriate excipient solutions (e.g., sucrose) as diluents. Appropriate dosages may be determined in clinical trails. The amount and frequency of administration will depend, of course, on such factors as the nature and severity of the indication being treated, the desired response, the condition of the patient, and so forth.

Soluble FcαR may be administered therapeutically, for example, as a vaccine adjuvant. Mucosal surfaces represent the body's largest area of contact with the environment and are thus the point of entry for numerous pathogens, ranging from the common cold to life-threatening infections such as AIDS. Vaccines would be most effective if they elicited the production of neutralizing or opsonizing IgA antibodies at the point of entry of the pathogen, i.e., at mucosal surfaces. Several studies in mice and humans have indicated that secretion of IgA from B cells can be up- or down-regulated by T cell derived IgA-binding factors. These binding factors represent soluble forms of IgA Fc receptors which act directly on B cells, thus regulating IgA production. A soluble form of the myeloid cell derived FcαR may serve a similar function, regulating IgA production. Thus, mucosal administration (orally, intranasally, etc.) of FcαR and a vaccine may be utilized to accentuate the development of antigen-specific IgA and improve protective immunity against that antigen.

Soluble FcαR which is administered therapeutically may also serve as an inhibitor of IgA-mediated phagocytosis. Previous studies have indicated that certain virus enter target cells through binding to FcγR. More specifically, antibody-coated viruses bind to cells (e.g., macrophages) by way of the Fc portion of the antibody molecule, triggering phagocytosis and uptake of the virus particle into the host cell. This mechanism has been proposed as a possible mode of entry of HIV into monocytes, which have been shown to be a long-term reservoir for the virus. In mucosal sites, FcαR-bearing effector cells may actually be prime candidates for uptake of virus by this mechanism. Recombinant FcαR (preferably in multimeric form such as in liposomes) may be used as a "sponge" for IgA-coated virus particles, thus diverting the antigen-antibody complex from uptake by effector cells. This would thus limit viral spreading in mucosal sites.

Within another embodiment, an anti-sense FcαR oligonucleotide is administered therapeutically to inhibit the production of FcαR in infected individuals. This therapy serves to remove binding sites for IgA-coated particles and prevent their uptake.

The following examples are offered by way of illustration, and not by way of limitation.

EXAMPLES

Example 1

A. cDNA Library Construction

Treatment of human histiocytic lymphoma cell line U-937 (American Type Culture Collection No. CRL 1593) with phorbol esters results in a dramatic upregulation of FcαR cell surface expression (see FIG. 5). The kinetics of receptor expression is analyzed by treating the cells with 5 ng/ml of PMA (phorbol myristate acetate), followed by analysis at various times for receptor expression. The cells are labeled with My43 (an anti-FcαR antibody obtained from Li Shen, see Shen et al., "My43, A monoclonal antibody that reacts with human myeloid cells inhibitors monocyte IgA binding and triggers function," J. Immun. 143(12):4117–22, December, 1989) and Flourescein Isothiocyanate (FITC) labeled anti-mouse IgM, and sorted with a FACScan Flow Cytometer (Becton Dickinson, Mountain View, Calif.). As shown in FIG. 6, mean fluorescence intensity increased in an approximately linear fashion between 8 and 22 hours after exposure to PMA. Due to the fact that increased mRNA levels precede protein expression, a time point at 12 hours is chosen for RNA preparation.

U-937 cells are treated for 12 hours with PMA (5 ng/ml), and then harvested. RNA is then extracted, and purified with an Oligo-dT column. Double-stranded cDNA synthesis is performed according to standard procedures using an Amersham cDNA synthesis kit (Amersham Corp., Arlington Heights, Ill.) (see March et al., Nature 315:641, 1985). After reverse transcription using oligo dT as primer, the single-standard cDNA is rendered double-stranded with DNA polymerase I and blunt-ended with T4 DNA polymerase.

Concurrently, a modified version of the pDC302 expression plasmid (see Mosely et al., Cell 59:335–48, 1989) is prepared. pDC302 contains regulatory sequences from SV40, adenovirus-2, and human cytomegalovirus. pDC302 containing a human IL-7 receptor insert has been deposited with the American Type Culture Collection (ATCC) under the name pCAV/NOT-IL-7R and assigned accession no. 68014. pDC302 is modified as follows. First, the intron present in the adenorirus tripartite leader sequence is deleted by replacing a Pvu II to Sca I fragment spanning the intron with the following synthetic oligonucleotide pair:

5'-CTGTTGGGCTCGCGGTTGAGGACAACTCTTCGC
GGTCTTTCCAGT-3'

3'-GACAACCCGAGCGCCAACTCCTGTTGAGAAGCG
CCAGAAAGGTCA-5'

This new plasmid is designated pDC303. Next, the plasmid is digested with Bgl II in the multiple cloning site. The plasmid and cDNA are then modified with the following linkers:

20-mer: AGCAGGTCGTCTCGTTCCAA
24-mer: GATCTTGGAACGAGACGACCTGCT

Because the linkers on the cDNA and plasmid are relatively long and complementary (but not self-complementary), cDNA and plasmid are easily ligated together.

Ligated DNA is used to transform E. coli (DH5α, BioRad Laboratories, Richmond, Calif.), generating a library which represents approximately 600,000 independent clones. The library is amplified by growing bacteria in liquid cultures in the presence of chloramphenicol overnight, then plating at a density of 5,000 colonies per plate. Colonies are scraped from plates and pooled, and plasmid DNA is recovered and purified by alkaline lysis and CsCl gradient centrifugation (see Sambrook et al., *Molecular Cloning: A Laboratory Manual,* 2d ed., 1989).

B. Transfection Expression and Immunoselection

Plasmid DNA (5 ug/10 cm culture dish) from the cDNA library is used to transfect a subconfluent layer of monkey COS-7 cells (ATCC No. CRL 1651) using DEAE dextran followed by chloroquine treatment, substantially as described by Luthman et al., (Nucl. Acids Res. 11:295, 1983) and McCutchan et al. (*J. Natl. Cancer Inst.* 41:351, 1968). Twelve plates of cells are grown for three days to permit transient expression of the inserted sequences. Immunoselection is accomplished essentially according to the method of Seed and Arrufo (*Proc. Natl. Acad. Sci. U.S.A.* 84:3365–3369, 1984). The cell monolayers are removed by incubation for 30 minutes at 37° C. in PBS/500 uM EDTA/0.02% sodium azide (PEA) and pooled. Following an additional PEA wash, cells are resuspended in 10 ml of PEA containing 5% heat-inactivated fetal calf serum (PEA/FCS) and a 1:50 dilution of My43 (anti-FcαR) hybridoma supernatant. After incubating cells for 1 hour on ice, cells are separated from unbound antibody on Ficoll gradients (2% Ficoll in PEA). Cell pellets are resuspended in PEA/FCS, and added to antiIgM pan plates. Briefly, pan plates are prepared by adding 3 ml of 2 ug/ml affinity-purified goat anti-murine IgM (Mu-chain specific; Organon Teknika, Durham, N.C.) in 50 mM Tris, pH 9.5 to 6 cm petri dishes (Falcon 1007). Plates are incubated for approximately 2 hours at room temperature and washed three times with PBS. Three ml of bovine serum albumin (1 mg/ml in PBS) is added and plates are incubated overnight at 4° C. Plates are aspirated and stored at −20° C. for no more than two weeks before use.

The cells are incubated in the anti-IgM pan plates for three hours at room temperature, after which unbound cells are removed by gently rinsing several times with PEA/FCS and PEA.

C. Extraction of DNA

Four hundred μl of lysing buffer containing sodium dodecyl sulfate (SDS) is added to each pan plate and incubated for 20 minutes at room temperature. Lysates are transferred from each dish to individual microfuge tubes containing 100 μl of 5M NaCl. The tubes are capped, inverted 20 times, and stored overnight at 4° C. High molecular weight DNA is removed by centrifugation. Following the addition of 2 μg of glycogen to each supernatant, preparations are extracted two times with phenol/chloroform and once with chloroform/isoamyl alcohol. Plasmid DNA is ethanol precipitated, washed with 70% ethanol, and vacuum dried. Following resuspension of pellets in water, the DNA is further purified by microdialysis against water and vacuum dried. The purified DNA is then transformed into *E. coli* by electroportion and plated on ampicillin plates. A large-scale transformation is carried out in this manner and plated, yielding 4–500,000 independent colonies (sublibrary 1). Colonies are removed from plates, pooled, amplified, and DNA is purified as described above.

D. Transfection and Immunoselection: Round II

Twelve COS cell plates are transfected with sublibrary 1 plasmid DNA. All subsequent immunoselection and DNA purification steps are performed essentially as described above. Round II yields a sublibrary (sublibrary 2) of approximately 50,000 independent colonies.

E. Spheroplast Fusion and Immunoselection: Round III

The third round of transfection involves fusion of bacterial spheroplasts with COS cells, a method which offers the advantage of transferring a more limited number of different plasmids per COS cell. Bacteria transformed with sublibrary 2 plasmids are grown overnight in chloramphenicol to amplify plasmid copy number.

1. Spheroplast Preparation

One hundred ml of bacterial cells are harvested by centrifugation and resuspended in 5 ml of cold 20% sucrose/50 mM Tris, pH 8.0. One ml of 5 mg/ml lysozyme in 0.25 M Tris, pH 8.0, is added and incubated for 5 minutes at 4° C. The enzymatic reaction is inhibited by the addition of two ml of 0.25 M EDTA, pH 8.0 and incubation for 5 minutes at 4° C. Two ml of 50 mM Tris, pH 8.0 is added, the spheroplasts are incubated for 5 min. at 37° C., then placed on ice. Spheroplast conversion is checked by microscopic examination.

2. Spheroplast Fusion

Twenty ml of cold DMEM containing 10% sucrose/10 mM magnesium chloride is added to spheroplasts. Five ml/plate of spheroplast suspension is added to 6 cm tissue culture plates containing semiconfluent COS-7 cells. Plates are centifuged at 10,000 xg for 10 minutes then supernatant fluid is carefully removed. Two ml of polyethylene glycol (PEG 1450) is carefully added to the cell layers, removed after 2–2.5 minutes, then plates are carefully washed three times with DMEM. Cells are incubated in DMEM/10% fetal calf serum containing antibiotics for 3–4 hours at 37° C. in 5% $CO_2$. Culture medium is replaced and cells are incubated for three days.

3. Immunoselection

Panning and episomal DNA purification as described above yields a sublibrary of 20,000 plasmids.

F. Pool Transfection and Immunoselection

Final screening for individual FcαR+ clones is conducted as follows. First, 96 individual colonies are picked from the Round III sublibrary, cultured overnight in a 96-well microtiter plate containing L-broth, and assembled into 20 pools. Plasmid DNA is prepared from each of the twenty pools and used to DEAE-transfect COS-7 cells. After three days in culture, the COS cells are harvested and analyzed for FcαR expression by two criteria: 1) My43 binding as measured by flow cytometry, and 2) rosette formation with IgA-coated ox red blood cells.

1. My43 (Anti-FcαR) Binding to Transfected COS Cells

COS cells transfected with pooled DNAs are incubated on ice for 30 minutes in the presence of the My43 monoclonal antibody or an isotype control. After washing twice, cells are incubated with fluoresceinated goat-anti mouse IgM (affinity purified F(ab')$_2$, TAGO, Burlingame, Calif.) for 30 minutes, and washed again. Cells are analyzed for FcαR expression by flow cytometry. Eleven pools (of 18 assayed) are positive in this assay.

2. IgA Rosette Formation

IgA rosette formation is accomplished essentially according to the method of Shen et al., supra. Briefly, 10 μl of packed ox red blood cells (ORBC) are mixed for 16 hours at 10° C. with 20 μl of either IgA or IgG derived from human myeloma patients. The cells are washed in RPM1 and adjusted to 1% (vol/vol).

Transfected COS cells ($3 \times 10^6$/ml) are then incubated with an equal volume (25 μl) of ox red blood cells (1% vol/vol). The cells are centrifuged together and incubated on ice for 90 minutes.

After gentle resuspension, the mixture is examined for the formation of rosettes by light microscopy. Eleven of eighteen pools bound IgA-coated ORBCs, whereas 0/18 bound IgG coated ORBCs. The eleven positive pools corresponded to the positives identified by flow cytometry as described above.

In addition, each of these eleven pools is found to contain at least one recombinant plasmid containing a 1.6 kb insert, as determined by Bgl II restriction analysis of pooled plasmid DNA. One of these pools is then broken down to eight individual clones, DNA is prepared from each, and COS-7 cells are transfected and assayed as above. Two out of eight clones are positive by flow cytometry, rosette formation, and the presence of the 1.6 kb insert. None of the other six isolates is positive by any of these criteria. DNA from one of the two positive clones is selected for all subsequent studies.

Example 2

Binding Specificity of FcαR-Transfected COS Cells

One clone, pHuFcαR, is selected for further analysis. COS cells are transfected either with empty vector or with pHuFcαR, then analyzed for binding of My43 or a control mAb (anti-murine IgM-FITC used as detecting reagent). The flow cytometry profiles in FIGS. 7A and 7B indicate that My43 binds to pHuFcαR-transfected COS cells, but not to control cells. Thus, the epitope recognized by My43 is found only on pHuFcαR transfected cells.

In order to show that this epitope is associated with an IgA binding protein, cells are incubated with FITC-IgA or FITC-IgG and analyzed by flow cytometry. As shown in FIGS. 7C and 7D, pHuFcαR-transfected cells bind human IgA, but not IgG. As expected, control COS cells fail to bind either isotype.

COS cells transfected with pHuFcαR also form distinct rosettes when incubated in the presence of human IgA-coated ox erythrocytes (see FIG. 8A), whereas sham-transfected COS cells do not (FIG. 8C). This activity is inhibited by the My43 mAb and human IgA, but not by human IgG (now shown). As a further indication of target specificity, the FcαR-transfected COS cells fail to form rosettes with human IgG-coated ox-erythrocytes (FIG. 8B). Thus, the recombinant receptor is capable of initiating the first step in IgA-mediated immune effector functions-specific binding of IgA-coated targets.

Example 3

Sequence Analysis

The nucleotide sequence of the pHuFcαR cDNA insert is determined utilizing standard procedures (see Hattori and Sakai, Anal. Biochem. 152:232-238, 1986). Briefly, E. coli containing the pHuFcαR clone is grown in two 10 ml cultures, and plasmid DNA prepared by the alkaline lysis method. Both sense and antisense strands are sequenced by the Sanger Dideoxy-mediated chaintermination method (see Sanger et al., Proc. Natl. Acad. Sci. U.S.A. 74:5463, 1977; see also Sambrook et al., supra at p. 13.42 et. seq.).

The nucleotide sequence of the pHuFcαR cDNA insert (FIG. 2) is composed of a 39 bp 5' untranslated region, 861 bp open reading frame, and a 711 bp 3' untranslated region terminating in a poly-A tract. The 3' region also includes an Alu repetitive sequence (approximately 1020-1300) and AT-rich stretches.

Example 4
Northern Blot Analysis

Northern bolts are accomplished using standard techniques (see Sambrook et al., supra, p. 7.39 et. seq.). Briefly, RNA is extracted from human cells, electrophoresed, and transferred to nitrocellulose filters. Filters are hybridized with a $^{32}$P-labeled antisense riboprobe generated as described (Promega Biotec) using a template a truncated version of pHuFcαR representing the 5' 728 nucleotides.

Two major hybridizing transcripts of approximately 2.8 kb and 2.6 kb are observed in polyadenylated RNA preparations from U-937 cells, peripheral blood monocytes, and polymorphonuclear leukocytes. Monocytes and PMNs express an additional band of approximately 4.2 kb. PMA-stimulated U-937 cells express significantly higher FcαR message levels in comparison to unstimulated U-937 cells, which is consistent with the finding that U-937 cell surface FcαR protein expression is PMA-inducible (see Monteiro et al., J. Exp. Med. 171:597-613, 1990). Except for nonspecific binding to ribosomal RNA, the FcαR probe fails to hybridize with polyadenylated RNA from either untreated or mitogen stimulated tonsillar B or T cells, or with total RNA from human dermal fibroblasts (FIG. 9, lane 3), even after extended exposure of blots.

Example 5
Construction and Expression of a Soluble Recombinant Human FcαR The pHuFcαR plasmid is linearized with Asp718, which cuts in the vector to the 5' side of the cDNA insert. Two oligonucleotides are synthesized for use as primers in the polymerase chain reaction:

Primer 1:
5'                                              3'
GCTCGCGGTACCGGGCACAGATCTTGGAACGAGACGA Primer 2:
5'                                              3'
CGGAGCAGATCTTTAGATCAAGTTCTGCGTCGTGTAATCT The 5' end of Primer 1 starts with 12 random bases, followed by the first 25 nucleotides of the 5' sequence of the pHuFcαR insert, including the Bgl II restriction site. The 5' end of Primer 2 begins with 6 random bases followed by a Bgl II site. This is followed by reverse orientation, antisense sequences for a termination codon (TTA) and bases 726 to 702 of the pHuFcαR cDNA insert. The latter bases represent the coding sequence for the first two amino acids of the putative transmembrane region and the last 6 amino acids of the extracellular region. Purified template DNA (Asp 718 linearized pHuFcαR) and primers are incubated in the presence of dNTPs and Taq polymerase and subjected to 40 cycles of polymerase chain reaction in a Perkins-Elmer thermocycler. The reaction product is organically extracted, ethanol precipitated, and digested with Bgl II, generating a 724 bp fragment with overhanging Bgl II ends. The solFcαR fragment is purified and ligated into Bgl II linearized pDC303 plasmid. Plasmid DNA is transformed into E. coli, selecting for ampicillin resistance, and the resulting colonies are screened by restriction enzyme digestion. Plasmid DNA is purified from clones representing the soluble FcαR insert in both orientations [pSolIgAR(+) and pSolIgAR(−)].

Example 6
Biological Activity of Soluble Recombinant Human FcαR

The pSolIgAR plasmids are DEAE transfected into COS-7 cells and culture supernatants are collected after three days of culture. After tenfold concentration, culture supernatants are assayed for biological activity by two methods: inhibition of My43 binding, and inhibition of IgA-rosette formation.

A. Inhibition of My43 Binding

Serial dilutions of COS-7 supernatants are added to My43 (1:10 dilution of hybridoma culture supernatant) and incubated at room temperature for 30 minutes. These mixtures are than added to peripheral blood monocytes or phorbol myistate acetate-included U-937 cells and incubated at 4° C. for 30 minutes. The cells are pelleted and washed three times. Fluorescein-conjugated goat anti-mouse IgM (affinity-purified, F(ab')$_2$) is added to each pellet and incubated at 4° C. for 30 minutes. Cells are then pelleted and washed three times (Antibody diluent and wash solution is PBS/1% fetal calf serum/0.01% NaN$_3$). Stained cells are analyzed on a FACScan flow cytometer (Becton Dickinson, San Jose, Calif.) by utilizing a logarithmic fluorescence intensity scale.

Inhibition of binding by soluble FcαR-containing supernatant is measured as a decrease in mean fluorescence intensity in comparison to cells incubated without culture supernatant or with negative control culture supernatant. As shown in FIG. 10, supernatants from cells transfected with pSolIgAR(+) inhibited by My43 binding in a dose-dependent manner, whereas pSolIgAR(−) or pDC303 transfected COS supernatants had no inhibitory effect upon My43 binding.

B. Inhibition of IgA Rosette Formation

The ability of U-937 cells to form rosettes with human IgA-coated ox red blood cells (ORBC) is assayed in the presence and absence of COS supernatants. Briefly, ORBCs are coated with either humans IgA or human IgG as described in Example 1. Next, 12.5 ul of a 2% solution of HuIgA-ORBC or HuIgG1-ORBC is incubated with 12.5 ul of COS-7 supernatant for 30 minutes at room temperature. Twenty-five μl of PMA-induced U-937 cells is added to each tube and incubated for 15 minutes at room temperature. Cells are pelleted by low speed centrifugation, then incubated on ice for 2 hours. Inhibition of rosette formation is determined by light microscopy, by comparing the number of rosettes per 200 U-937 cells for cells treated in the presence or absence of COS-7 cell supernatants.

Results in Table 1 show that supernatants from cells transfected with pSolIgAR(+) inhibited IgA rosette formation, whereas pSolIgAR(−) or pDC303 transfected COS supernatants have no inhibitory effect. These results indicate that the pSolIgAR(+) direct the expression of a recombinant protein with the characteristics expected of a soluble FcαR.

TABLE 1

Inhibition IgA rosette formation by COS cell supernatants containing recombinant soluble FcαR.

| Supernatant* | % Rosette Forming Cells** |
| --- | --- |
| Medium | 57.7 |
| pSolIgAR(+) | 2.5 |
| pSOlIgAR(−) | 50.6 |
| pDC303 | 57.0 |

*Supernatants form COS cells transfected with the indicated plasmids are sterile filtered and concentrated 10X. IgA-coated ox erythrocytes are pre-incubated in the presence of concentrated supernatants prior to the addition to PMA-induced U-937 cells.
**Rosette formation is assessed by counting the percentage of U-937 cells which have at least three red cells attached. A total of 200 U-937 cells are counted per condition.

C. Immunoprecipitation Of The Soluble Recombinant human FcαR

The molecular size of the recombinant FcαR agrees with the predicted molecular weight, as indicated in the following experiment. After three days in culture, transfected COS cells are labeled for 6 hours with $^{35}$S-methionine and supernatants are collected. The supernatants are subjected to immunoprecipitation with the My43 mAb, followed by SDS-PAGE analysis and autoradiography. Results in FIG. 11 indicate that My43 (lane F), but not a control IgM mAb (lane E), immunoprecipitate a protein represented by a broad band of 32-45 kD from pSolIgAR(+) supernatants. The diffuse nature of the protein band probably represents differential glycosylation of the peptide backbone. In contrast, supernatants from COS cells transfected with pSolIgAK(−) (lanes C, D) or with pDC303 (lanes A, B) display no unique bands following immunoprecipitation.

Example 7

Isolation Of The Murine IgA Fc Receptor

E. coli is transfected with the pSolIgAR(+) plasmid and grown to late log phase in TB (Terrific Broth). The bacteria are harvested by centrifugation, and the plasmid DNA recovered by alkaline lysis and CsCl gradient centrifugation as described above. The insert is excised with Bgl II, and purified by agarose gel electrophoresis. Insert DNA is then $^{32}$P labeled using a random primer labeling kit (Pharmacia, Uppsala, Sweden).

A cDNA library is prepared from a mouse thymoma, whose mRNA had previously been shown to hybridize in a Northern blot to the $^{32}$P labelled DNA probe. Briefly, total cellular RNA is obtained from a mouse cell line such as EL4 (ATCC No. TTB 39), or 1C9 (obtained from Richard Lynch, University of Iowa).

Poly(A)+ RNA was isolated by oligo(dT)-cellulose chromatography, and used to construct an oligo(dT)-primed cDNA library in the bacteriophage λ gt11 using standard techniques (see, Sambrook et al., supra).

Duplicate nitrocellulose filter lifts from plates containing recombinant phage plaques are screened with the above described $^{32}$P labeled DNA probe, subjected to washing conditions at a stringency of 55° C., 6× SSC, and then subjected to autoradiography overnight. Positive plaques are pulled, and subjected to additional cycles of enrichment as described above.

Following several cycles of enrichment, several hybridizing clones are isolated. E. coli infected with the positive phage plaques are amplified in culture. Phage DNA is then purified by standard techniques (see, Sambrook et al, supra). A southern blot is performed to ensure that the insert hybridized to the DNA probe. The cDNA clone is then sequenced by the dideoxynucleotide chain termination method (see Sanger et al., Proc. Natl. Acad. Sci. USA 74:5463-5467, 1977), yielding the sequence for the murine IgA Fc receptor.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. An isolated DNA selected from the group consisting of:
   (a) cDNA clones having a nucleotide sequence encoding a protein having an amino acid sequence of amino acids 1 through 266 of FIG. 2;
   (b) isolated DNA capable of hybridization to a clone of (a) under moderately stringent conditions and which encode biologically active IgA Fc receptor protein; and
   (c) isolated DNA which is degenerate as a result of the genetic code to the DNA defined in (a) or (b) and which encode biologically active IgA Fc receptor protein.

2. An isolated DNA comprising the sequence of nucleotides 1 to 900, as depicted in FIG. 2.

3. An isolated DNA comprising the sequence of nucleotides 40 to 720, as depicted in FIG. 2.

4. A recombinant expression vector comprising the DNA according to claim 1.

5. A recombinant expression vector comprising the DNA according to claim 2.

6. A recombinant expression vector comprising the DNA according to claim 3.

7. A host cell containing a recombinant expression vector according to claim 4.

8. A host cell containing a recombinant expression vector according to claim 5.

9. A host cell containing a recombinant expression vector according to claim 6.

10. A method for preparing an IgA Fc receptor, comprising culturing a suitable host cell according to claim 8, under conditions promoting expression.

11. A method for preparing a soluble IgA Fc receptor, comprising culturing a suitable host cell according to claim 9, under conditions promoting expression.

* * * * *

UNITED STATES PATENT AND TRADEMARK OFFICE
CERTIFICATE OF CORRECTION

PATENT NO. : 5,198,342
DATED : March 30, 1993
INVENTOR(S) : Maliszewski, Charles R.

It is certified that error appears in the above-identified patent and that said Letters Patent is hereby corrected as shown below:

At column 3, line 20, delete the letter [C] after its second occurence and insert -- D --.

At column 4, line 28, delete the word [Examplary] and insert --Exemplary--.

At column 9, line 15, delete [Redcombinant] and insert -- Recombinant --.

At column 11, line 8, delete [stain] and insert -- strain --.

At column 11, line 23, delete [amutant] and insert the words -- a mutant --.

Signed and Sealed this

Twenty-third Day of November, 1993

Attest:

BRUCE LEHMAN

Attesting Officer

Commissioner of Patents and Trademarks